US012796900B2

(12) United States Patent
Shie

(10) Patent No.: US 12,796,900 B2
(45) Date of Patent: Nov. 17, 2026

(54) ENDOSCOPE DEVICE WITH A SUPPORT MECHANISM

(71) Applicant: Chang-Bih Shie, Tainan City (TW)

(72) Inventor: Chang-Bih Shie, Tainan City (TW)

( * ) Notice: Subject to any disclaimer, the term of this patent is extended or adjusted under 35 U.S.C. 154(b) by 6 days.

(21) Appl. No.: 18/853,074

(22) PCT Filed: Apr. 17, 2023

(86) PCT No.: PCT/CN2023/088596
§ 371 (c)(1),
(2) Date: Sep. 30, 2024

(87) PCT Pub. No.: WO2023/207645
PCT Pub. Date: Nov. 2, 2023

(65) Prior Publication Data

US 2025/0213098 A1 Jul. 3, 2025

(30) Foreign Application Priority Data

Apr. 27, 2022 (CN) ......................... 202210448463.9

(51) Int. Cl.
*A61B 1/00* (2006.01)
*A61B 1/005* (2006.01)
*A61B 1/05* (2006.01)

(52) U.S. Cl.
CPC ........ *A61B 1/0055* (2013.01); *A61B 1/00119* (2013.01); *A61B 1/00128* (2013.01); *A61B 1/00131* (2013.01); *A61B 1/05* (2013.01)

(58) Field of Classification Search
CPC ... A61B 1/00064; A61B 1/005; A61B 1/0053; A61B 1/0055; A61B 1/01; A61B 1/00078
See application file for complete search history.

(56) References Cited

U.S. PATENT DOCUMENTS 5,688,221 A * 11/1997 Yabe ...................... A61B 1/042 600/139
5,733,245 A * 3/1998 Kawano ............... A61B 1/0052 600/146

(Continued)

FOREIGN PATENT DOCUMENTS

CN 102789049 A 11/2012
CN 102789050 A 11/2012

(Continued)

OTHER PUBLICATIONS

Search Report issued in TW application No. 111115935 dated Jul. 6, 2023.

(Continued)

*Primary Examiner* — Timothy J Neal
(74) *Attorney, Agent, or Firm* — HSML P.C.

(57) ABSTRACT

An endoscope device includes a tubular mechanism and a control mechanism connected with the tubular mechanism. The tubular mechanism includes an elongated body, a camera lens unit mounted at a distal end of the elongated body, and a support unit including a support bracket securely disposed in a lumen of the elongated body and extending along a longitudinal axis. The support bracket is flexibly bendable and is controlled to be bent sideways so as to bend the elongated body and steer insertion of the distal end of the tubular wall into a body's cavity. A sufficient axial force is provided to the tubular mechanism during the insertion of a medical tube with the endoscope device so as to facilitate the insertion procedure of the tube.

18 Claims, 9 Drawing Sheets

(56) References Cited

U.S. PATENT DOCUMENTS

| | | | | |
|---|---|---|---|---|
| 2007/0233040 | A1* | 10/2007 | Macnamara ......... | A61B 1/0055 604/523 |
| 2013/0310640 | A1 | 11/2013 | Hashiba et al. | |
| 2021/0330175 | A1* | 10/2021 | Kühn ................... | A61B 1/0055 |

FOREIGN PATENT DOCUMENTS

| | | | |
|---|---|---|---|
| CN | 203204237 | U | 9/2013 |
| CN | 110833385 | A | 2/2020 |
| CN | 114795064 | A | 7/2022 |
| JP | H03-128028 | A | 5/1991 |
| JP | 2000-262464 | A | 9/2000 |
| JP | 2009-018044 | A | 1/2009 |
| KR | 20190106758 | A | 9/2019 |
| TW | M396102 | U | 1/2011 |
| TW | 201231004 | A | 8/2012 |
| TW | 201350076 | A | 12/2013 |
| TW | 201436756 | A | 10/2014 |
| TW | 202015610 | A | 5/2020 |
| WO | 2015033602 | A1 | 3/2015 |

OTHER PUBLICATIONS

International Search Report for International Application No. PCT/CN2023/088596 mailed Jul. 19, 2023.

* cited by examiner

ENDOSCOPE DEVICE WITH A SUPPORT MECHANISM

CROSS-REFERENCE TO RELATED APPLICATIONS

This application is a national stage filing under 35 U.S.C. 371 of International Application No. PCT/CN2023/088596, filed on Apr. 17, 2023, which claims priority to Application No. 202210448463.9, filed Apr. 27, 2022, in China. The entire teachings of the above applications are hereby incorporated by reference in their entirety. International Application No. PCT/US2023/088596 was published under PCT Article 21(2) in English.

FIELD

The disclosure relates to an endoscope device, and more particularly to an endoscope device with a support mechanism to facilitate insertion of an insertion tube.

BACKGROUND

A conventional endoscope has a flexible insertion tube with an axial support force provided only by the structural integrity of a tubular sheath. However, this support is quite weak and may be liable to bending and deformation during an insertion procedure. Hence, when the endoscope is used for a variety of treatment, such as for inserting a nasogastric tube into the stomach or the duodenum, or for passing a Foley catheter through the urethra and into the bladder, the insertion operation may be troublesome to perform due to insufficient axial support of the insertion tube.

SUMMARY

Therefore, an object of the disclosure is to provide an endoscope device that can alleviate at least one of the drawbacks of the prior art.

According to the disclosure, the endoscope device includes a tubular mechanism. The tubular mechanism includes an elongated body which has a tubular wall that defines a lumen therein and which extends along and surrounds a longitudinal axis. The tubular wall has a proximal end and a distal end opposite to each other along the longitudinal axis. A camera lens unit is mounted at the distal end of the tubular wall to capture images of an object in front thereof. A support unit includes a support bracket which is securely disposed in the lumen and which extends along the longitudinal axis. The support bracket is flexibly bendable and is controlled to be bent sideways so as to bend the elongated body and steer insertion of the distal end of the tubular wall into a patient's body cavity.

With the support bracket securely disposed in the elongated body of the tubular mechanism, a sufficient axial force is provided to the tubular mechanism during the insertion of a medical tube or catheter with the endoscope device so as to facilitate the insertion procedure of the tube or catheter.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
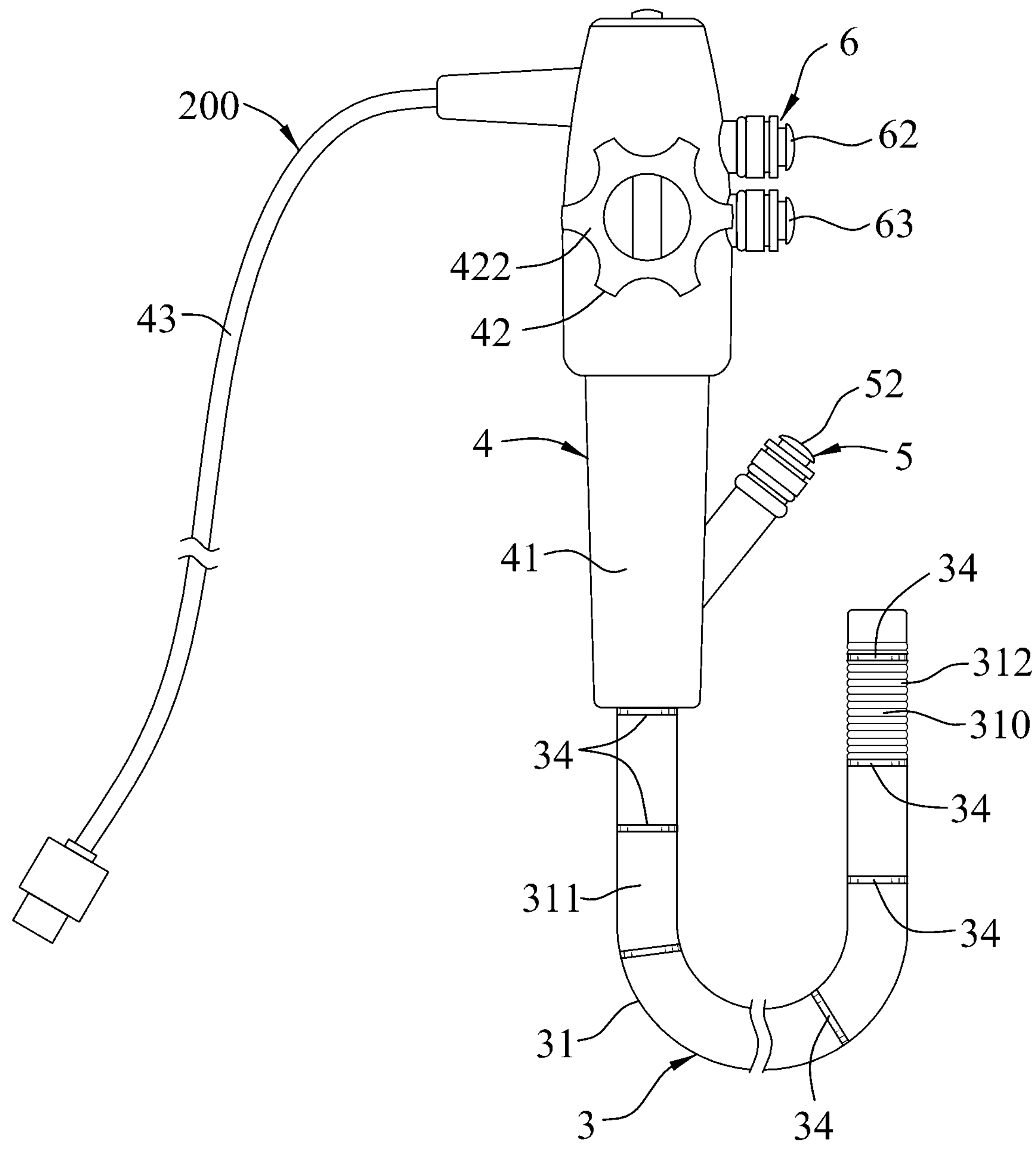
FIG. 1 is a schematic side view illustrating an embodiment of an endoscope device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently (e.g., rotated 90 degrees or at other orientations) and the spatially relative terms used herein may be interpreted accordingly.

Figure 2:
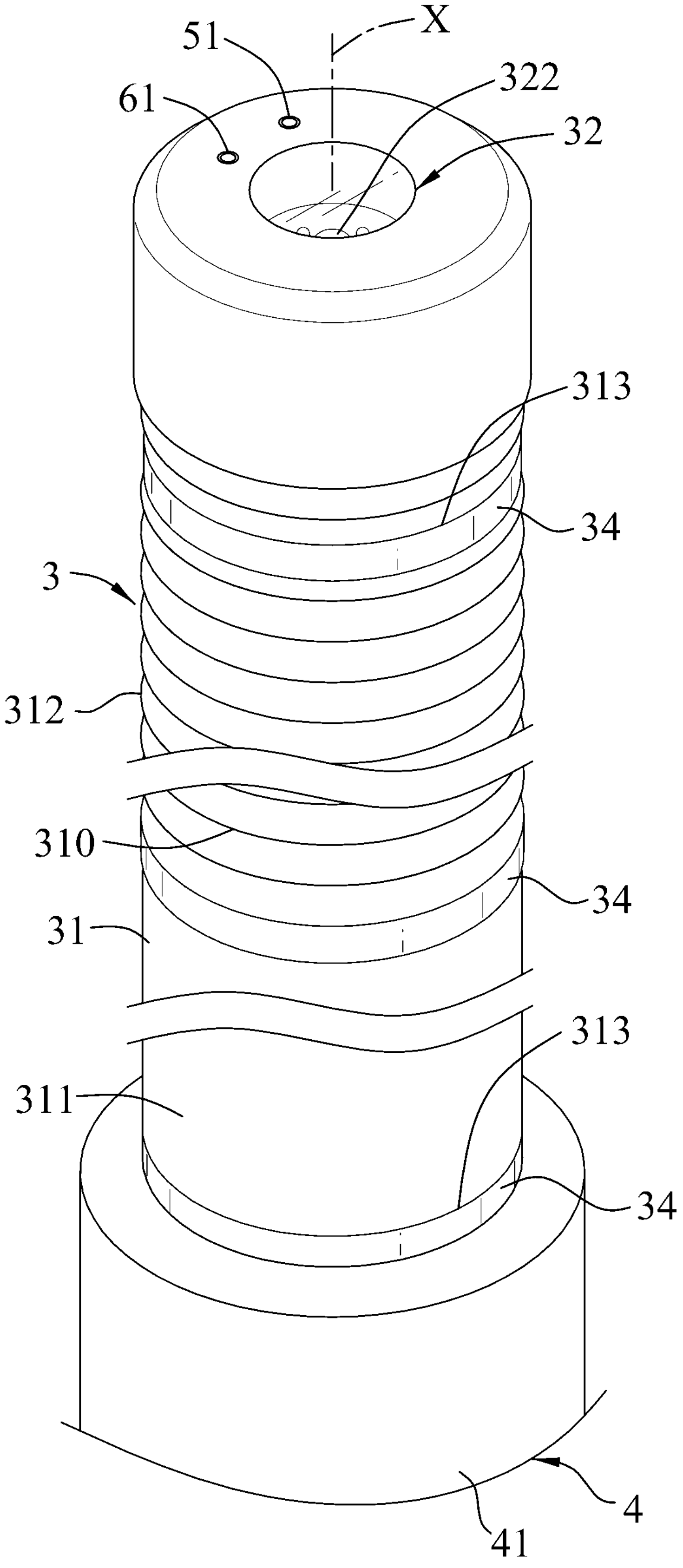
FIG. 2 is a fragmentary perspective view illustrating a tubular mechanism of the embodiment.
Figure 3:
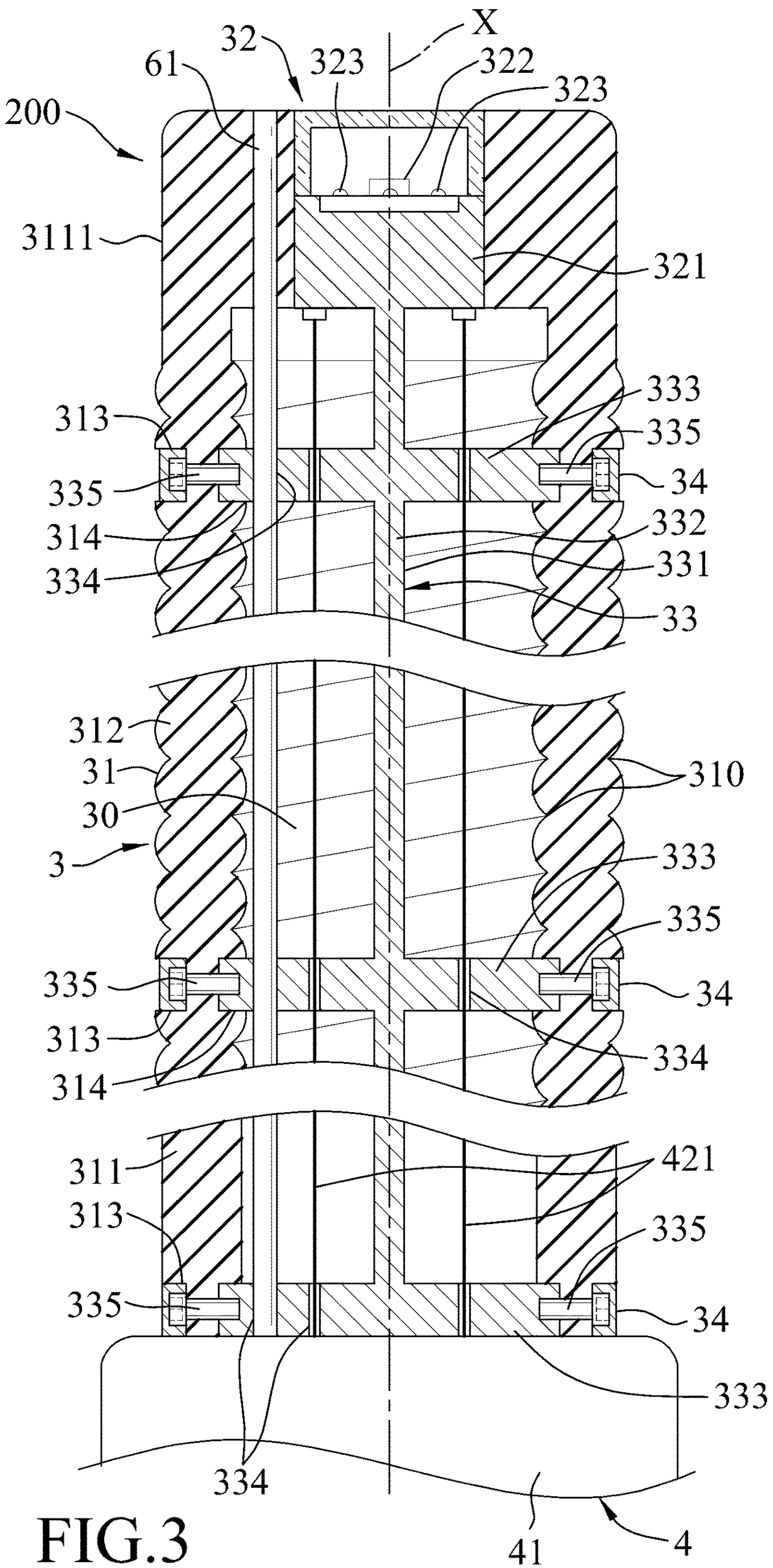
FIG. 3 is a fragmentary sectional view of the tubular mechanism.

Referring to FIGS. 1, 2 and 3, an embodiment of an endoscope device 200 according to the disclosure is for inserting a nasogastric tube into the stomach or the duodenum, or for passing a Foley catheter through the urethra and into the bladder. The endoscope device 200 includes a tubular mechanism 3, a control mechanism 4 which is connected with an end of the tubular mechanism 3, and a suction mechanism 5 and a fluid jetting mechanism 6 which are disposed on the tubular mechanism 3 and the control mechanism 4.

The tubular mechanism 3 includes an elongated body 31 which has a tubular wall 311 that defines a lumen 30 therein and which extends along and surrounds a longitudinal axis (X). The elongated body 31 is in the form of a catheter which is bendable and deformable. The tubular wall 311 has a proximal end and a distal end opposite to each other along the longitudinal axis (X). The tubular wall 311 has an end wall 3111 at the distal end, and a bending section 312 adjacent to the distal end and having threads 310 on outer and inner peripheral surfaces thereof such that the bending section 312 is more bendable than the remaining part of the tubular wall 311. Further, the tubular wall 311 has a plurality of outer annular grooves 313 which are recessed from the outer peripheral surface of the tubular wall 311, which surround the longitudinal axis (X), and which are spaced apart from each other in a direction of the longitudinal axis (X), and a plurality of inner annular grooves 314 which are recessed from the inner peripheral surface of the tubular wall 311, which surround the longitudinal axis (X), and which are spaced apart from each other in the direction of the longitudinal axis (X) to be respectively and radially opposite to the outer annular grooves 313. In one embodiment, the elongated body 31 is made of silicone rubber material, rubber material or other medical grade silicone.

The tubular mechanism 3 further includes a camera lens unit 32 exposed from the end wall 3111 of the tubular wall 311 to capture images of an object in front thereof. The camera lens unit 32 includes a lens mounting seat 321 which is securely disposed in the lumen 30 at the distal end 321, an image capturing element 322 which is mounted on the lens mounting seat 321, and a plurality of light emitting elements 323 which are mounted on the lens mounting seat 321. Since the camera lens unit 32 is of a known type in the field of endoscope technology, and may have a variety of different constructions, further description thereof is dispensed with for the sake of brevity.

Figure 4:
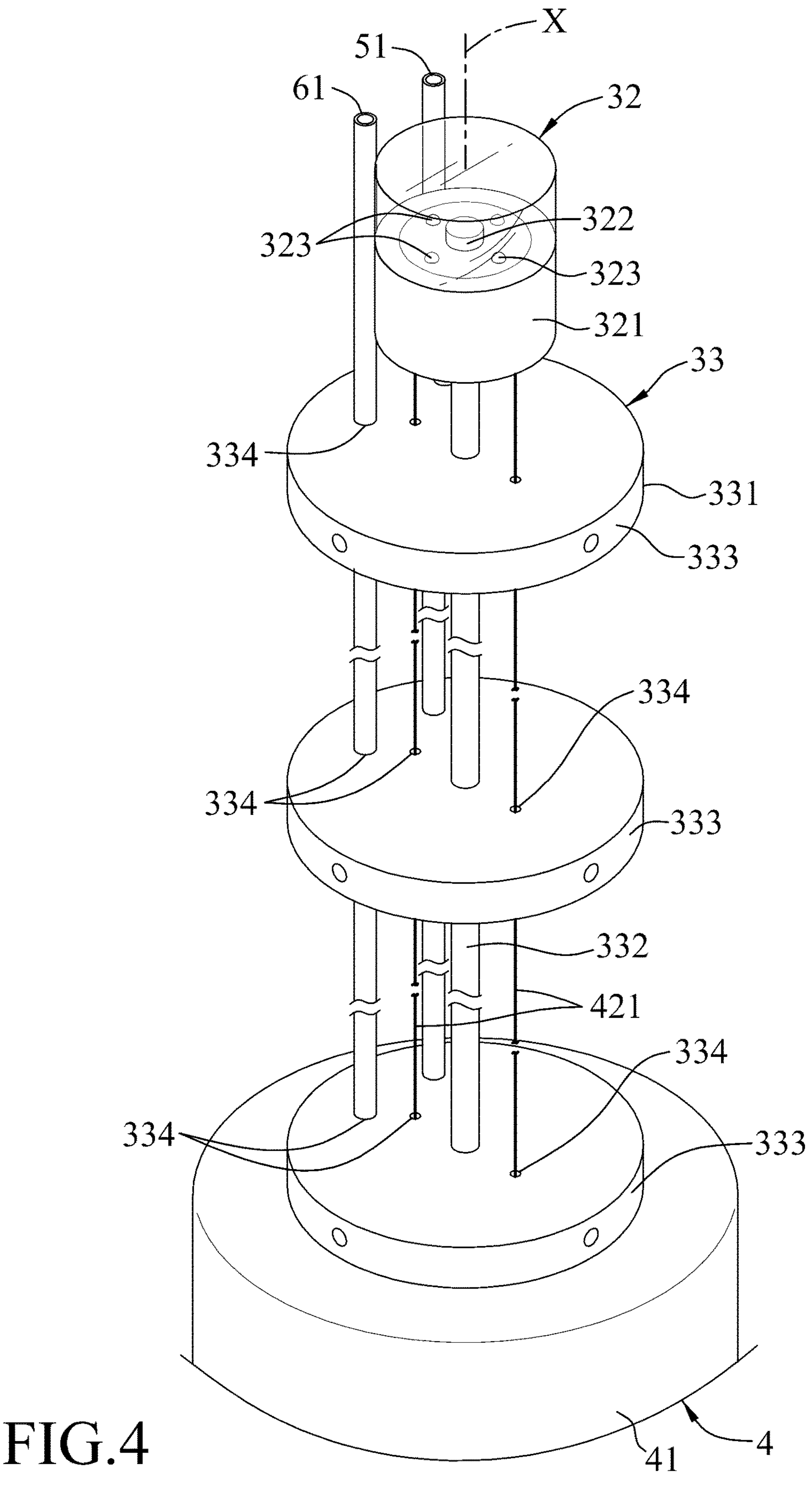
FIG. 4 is a fragmentary perspective view illustrating a support unit of the embodiment.

With reference to FIGS. 2, 3 and 4, the tubular mechanism 3 further includes a support unit 33. The support unit 33 includes a support bracket 331 which is securely disposed in the lumen 30 and which extends along the longitudinal axis (X), and a plurality of fasteners 335 which extend radially through the tubular wall 311 and which engage with the support bracket 331 to fasten the support bracket 331 to the tubular wall 311.

Specifically, the support bracket 331 has a support shaft 332 which extends along the longitudinal axis (X) to be spaced apart from the tubular wall 311, which is connected between the lens mounting seat 321 and the control mechanism 4, and a plurality of crosspieces 333 which extend radially from the support shaft 332, which are securely connected with the inner peripheral surface of the tubular wall 311 and which are spaced apart from each other along the longitudinal axis (X). The support shaft 332 is bendable sideways. Each crosspiece 333 is in the form of a disc, and has a peripheral rim which is securely fitted in the corresponding inner annular groove 314 of the inner peripheral surface of the tubular wall 311. The crosspieces 333 respectively have a plurality of wire holes 334 which are formed therethrough and respectively aligned with each other in the direction of the longitudinal axis (X).

Each of the fasteners 335 extends through the outer and inner annular grooves 313, 314 and is securely engaged with the corresponding crosspiece 333 to fasten the crosspiece 333 to the tubular wall 311. For example, the fastener 335 may be a screw fastener which extends radially through the tubular wall 311 and which is threadedly and removably engaged with the crosspiece 333. The fastener 335 has a head disposed in the outer annular groove 313 to expose therefrom. Thus, an engaging ring 34 is disposed in the outer annular groove 313 to conceal the fastener 335. The engaging ring 34 may be including, but not limited to, a silicone rubber material, and is disposed to prevent removal of the fasteners 335.

In one embodiment, the support shaft 332 is in the form of a solid shaft which is made of metal or plastic material, such as a shape-memory alloy. The crosspieces 333 may be made of a material that is the same or different from that of the support shaft 332. Further, the support shaft 332 is securely connected with or is integrally formed with the lens mounting seat 321. Alternatively, in other modified embodiments, the support shaft 332 is in the form of a hollow tubular shaft which is bendable sideways. Alternatively, the support shaft 332 may be in the form of a spring tube or a coil spring. Furthermore, the support shaft 332 may be removably and threadedly engaged with the lens mounting seat 321, or removably fitted to the lens mounting seat 321.

With reference to FIGS. 1, 3 and 4, the control mechanism 4 includes an operating handle 41 which is connected with the proximal ends of the elongated body 31 and the support shaft 332, a bending adjusting module 42 which is mounted on the operating handle 41 and which is connected with the support unit 33, and a universal cord 43 which is mounted on the operating handle 41 and in signal connection with the camera lens unit 32.

In one embodiment, the bending regulating module 42 has two pulling wires 421 which extend longitudinally through the aligning wire holes 334 of the crosspieces 333 and which are connected with the lens mounting seat 321, and a regulating knob 422 which is mounted outwardly of the operating handle 41 and which is connected with the pulling wires 421. The regulating knob 422 is operable to pull or release the pulling wires 421 to bend and deform the support bracket 331 sideways so as to bend the elongated body 31 and steer insertion of the distal end of the elongated body 31 into a patient's body cavity. Since the bending regulating module 42 is of a known type in the field of endoscope technology, and may have a variety of constructions, further description thereof is dispensed with for the sake of brevity.

The suction mechanism 5 includes a suction tube 51 which is disposed within the operating handle 41 and which extends in the lumen 30 in the direction of the longitudinal axis (X), and a suction valve 52 which is mounted on the operating handle 41 and which is connected and communicated with the suction tube 51. The suction tube 51 extends through the aligning wire holes 334, and has a front suction end projecting outwardly of the distal end of the elongated body 31. The suction valve 52 is connected with a suction device (not shown) to be operable to communicate the suction device with the suction tube 51 for performing suction of gas and fluid through the suction tube 51.

The fluid jetting mechanism 6 includes a jetting tube 61 which is disposed within the operating handle 41 and which extends into the lumen 30 in the direction of the longitudinal axis (X), and a water feeding valve 62 and an air feeding valve 63 which are mounted on the operating handle 41 and which are connected and communicated with the jetting tube 61. The jetting tube 61 extends through the aligning wire holes 334, and has a front jetting end projecting outwardly of the distal end of the elongated body 31. The water feeding valve 62 is connected with a water pump device (not shown) to be operable to communicate the water pump device with the jetting tube 61 for performing water jetting through the jetting tube 61. The air feeding valve 62 is connected with an air pump device (not shown) to be operable to communicate the air pump device with the jetting tube 61 for performing air jetting through the jetting tube 61.

Since the suction mechanism 5 and the fluid jetting mechanism 6 are of a known type in the field of endoscope technology, and may have a variety of constructions, further description thereof is dispensed with for the sake of brevity.

When the endoscope device of the embodiment is used for insertion of a tube or a catheter, such as a nasogastric tube, a Foley catheter, etc., the tubular mechanism 3 is inserted into the tube or catheter, and the tubular mechanism 3 and the tube are then inserted into the patient's body. With the support bracket 331 disposed in the elongated body 31 of the tubular mechanism 3, a sufficient axial force is provided during the insertion of the tube so as to facilitate the insertion procedure of the tube.

Figure 5:
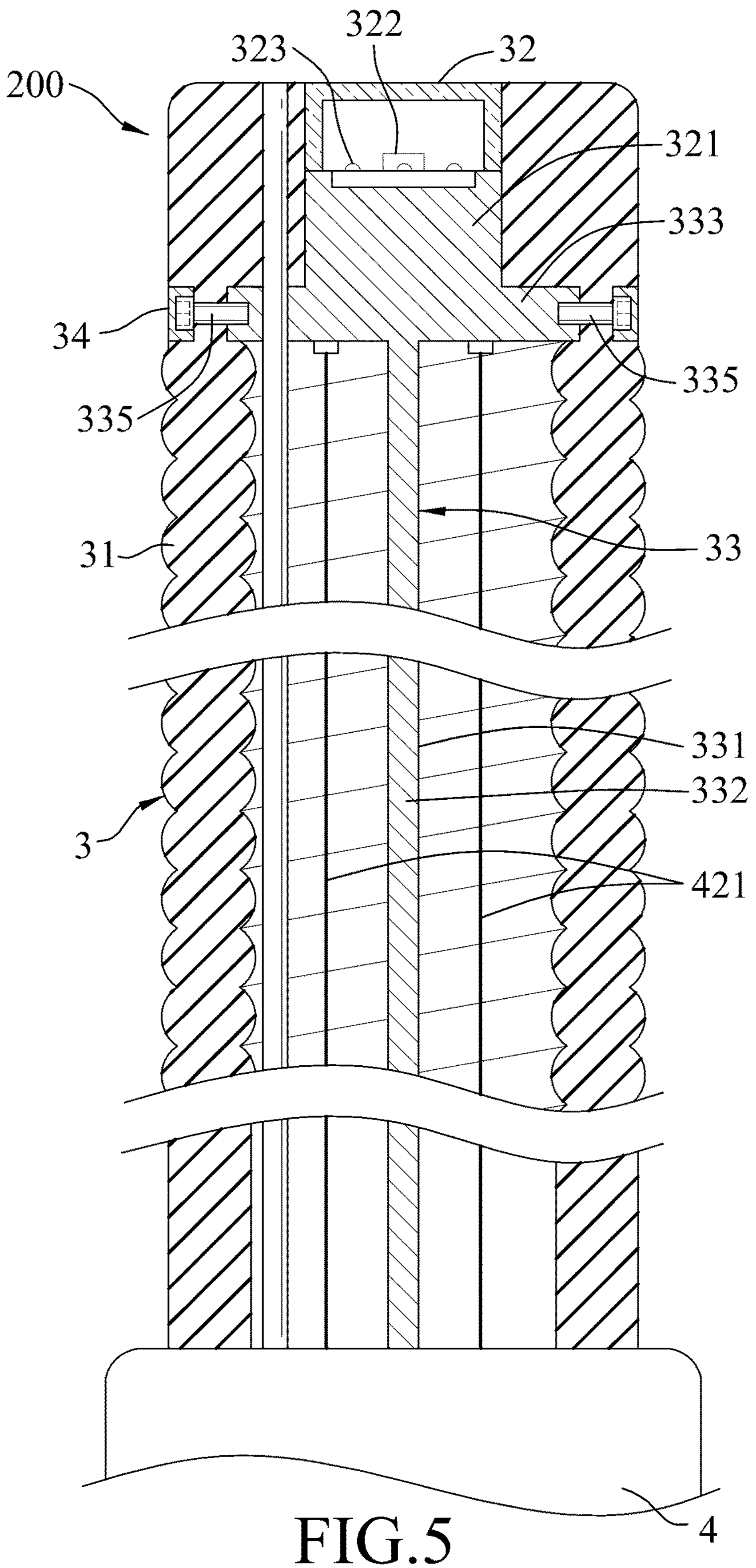
FIG. 5 is a view similar to FIG. 3, illustrating the tubular mechanism in a modified form.
Figure 6:
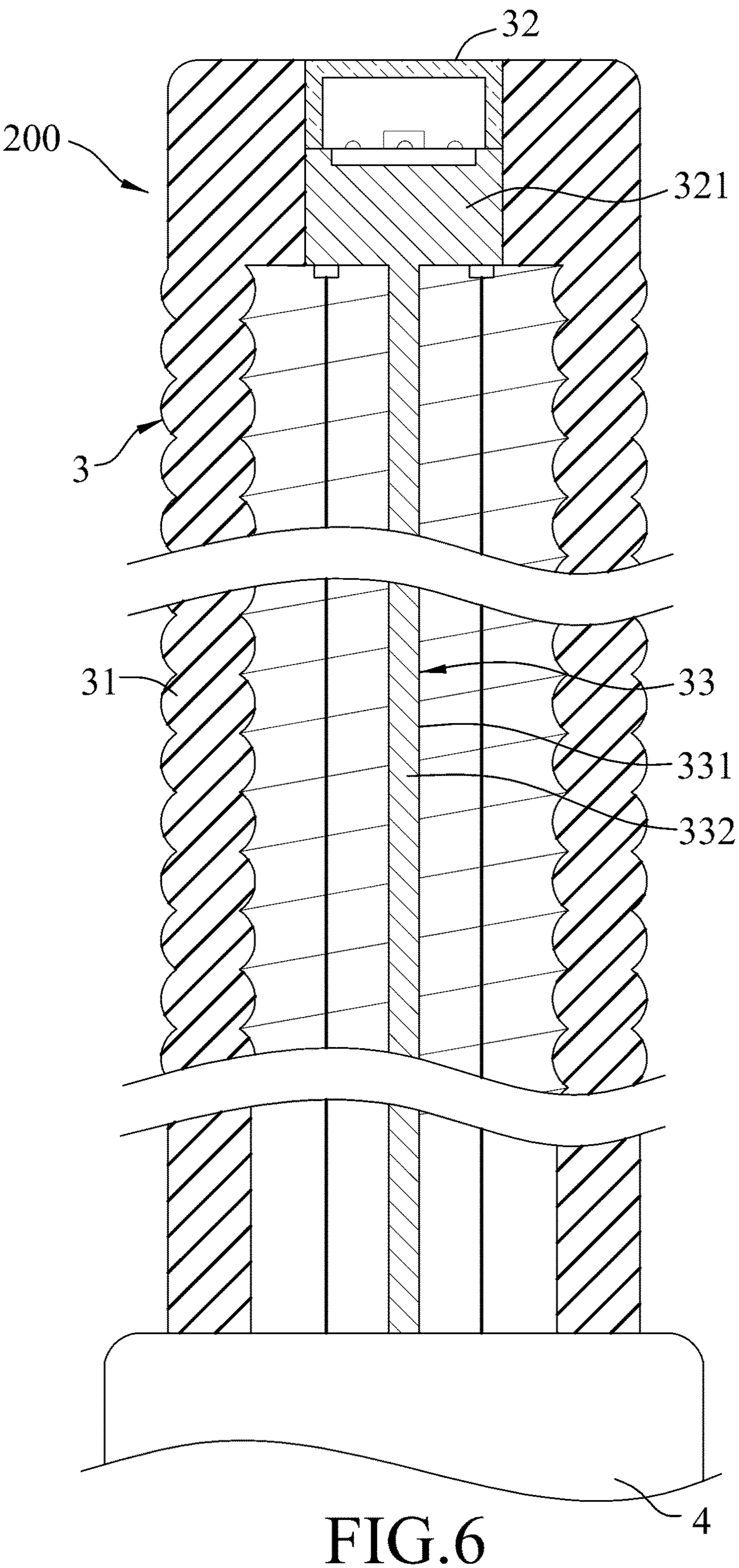
FIG. 6 is a view similar to FIG. 3, illustrating the tubular mechanism in another modified form.

With reference to FIG. 3, in one embodiment, the support bracket 331 has a plurality of the crosspieces 333 spaced apart from each other along the longitudinal axis (X) to improve the structural and connection strength of the elongated body 31 and the support bracket 331. In variants of the embodiment, the number of the crosspieces 333 may be varied as required. For example, the crosspieces 333 are disposed only at a proximal end or a middle portion of the support shaft 332 (as shown in FIG. 5). Alternatively, as shown in FIG. 6, the crosspiece 333 is dispensed with. Moreover, in one embodiment, the crosspiece 333 is disposed only at the proximal end of the support shaft 332, and is connected with the lens mounting seat 321. In this embodiment, the pulling wires 421 are securely connected with the crosspiece 333.

Figure 7:
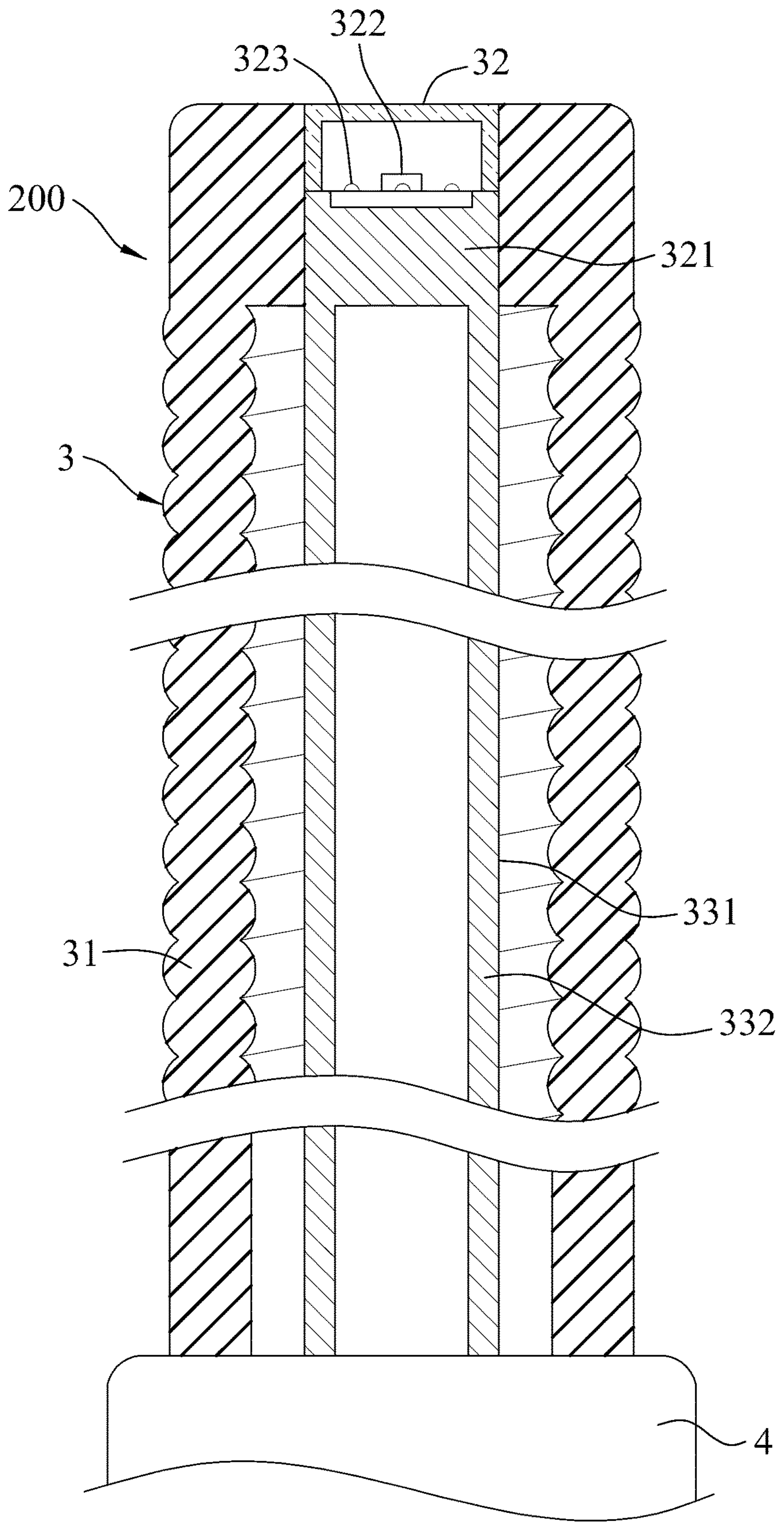
FIG. 7 is a view similar to FIG. 6, illustrating the tubular mechanism in a still another modified form.
Figure 8:
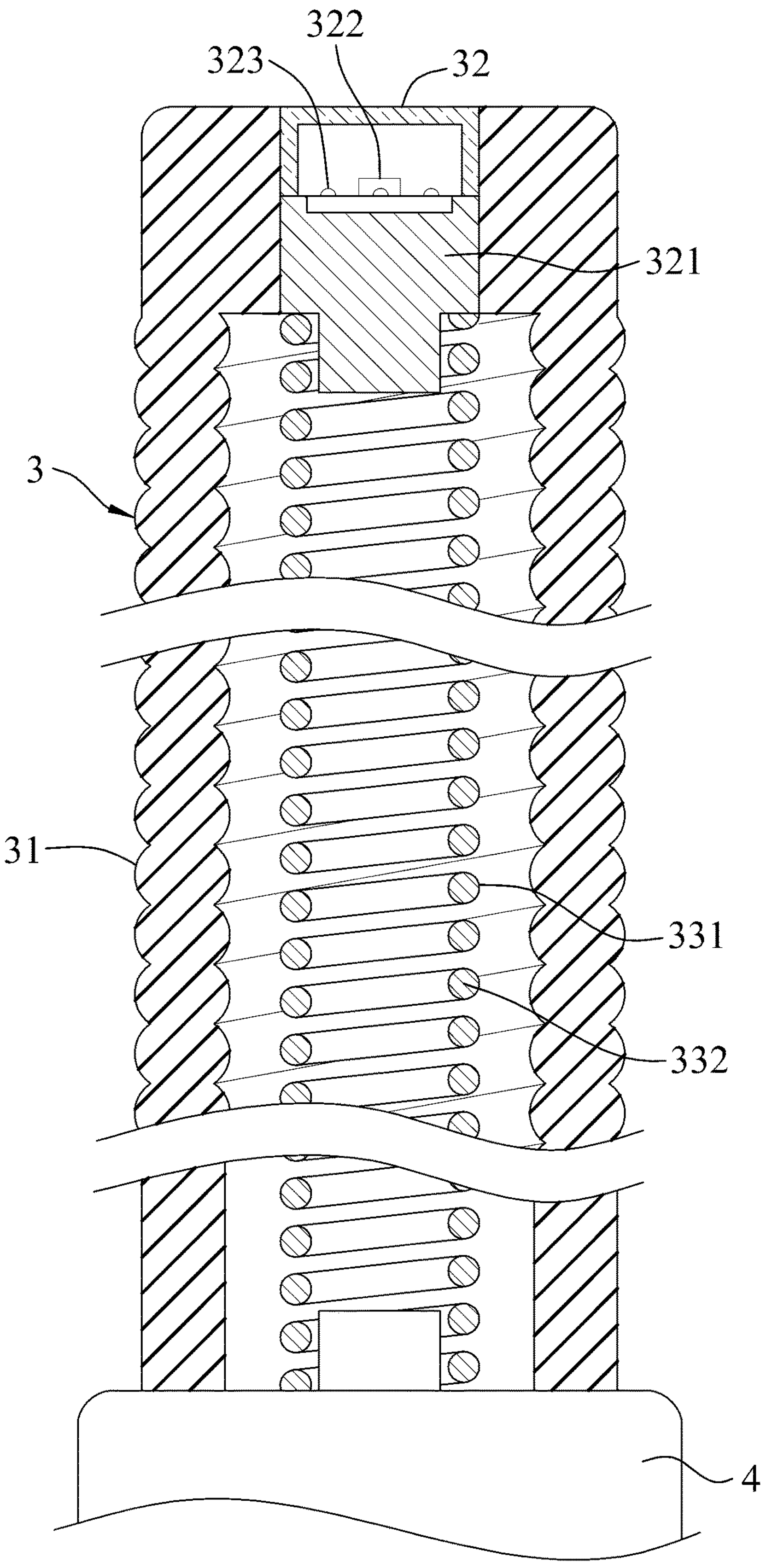
FIG. 8 is a view similar to FIG. 6, illustrating the tubular mechanism in yet another modified form.

In variants of the embodiment, the support shaft 332 is in the form of a flexible tubular shaft, as shown in FIG. 7. Alternatively, as shown in FIG. 8, the support shaft 332 is in the form of a spring tube or a coil spring.

Furthermore, the engaging rings 34 are disposed in the outer annular grooves 313 of the elongated body 31 to conceal the fasteners 335 and to prevent removal of the fasteners 335 during the insertion procedure of the tube. Alternatively, the elongated body 31 may be adhered with the crosspieces 333 of the support unit 33. Hence, the engaging rings 34 and the fasteners 335 are dispensed with.

Figure 9:
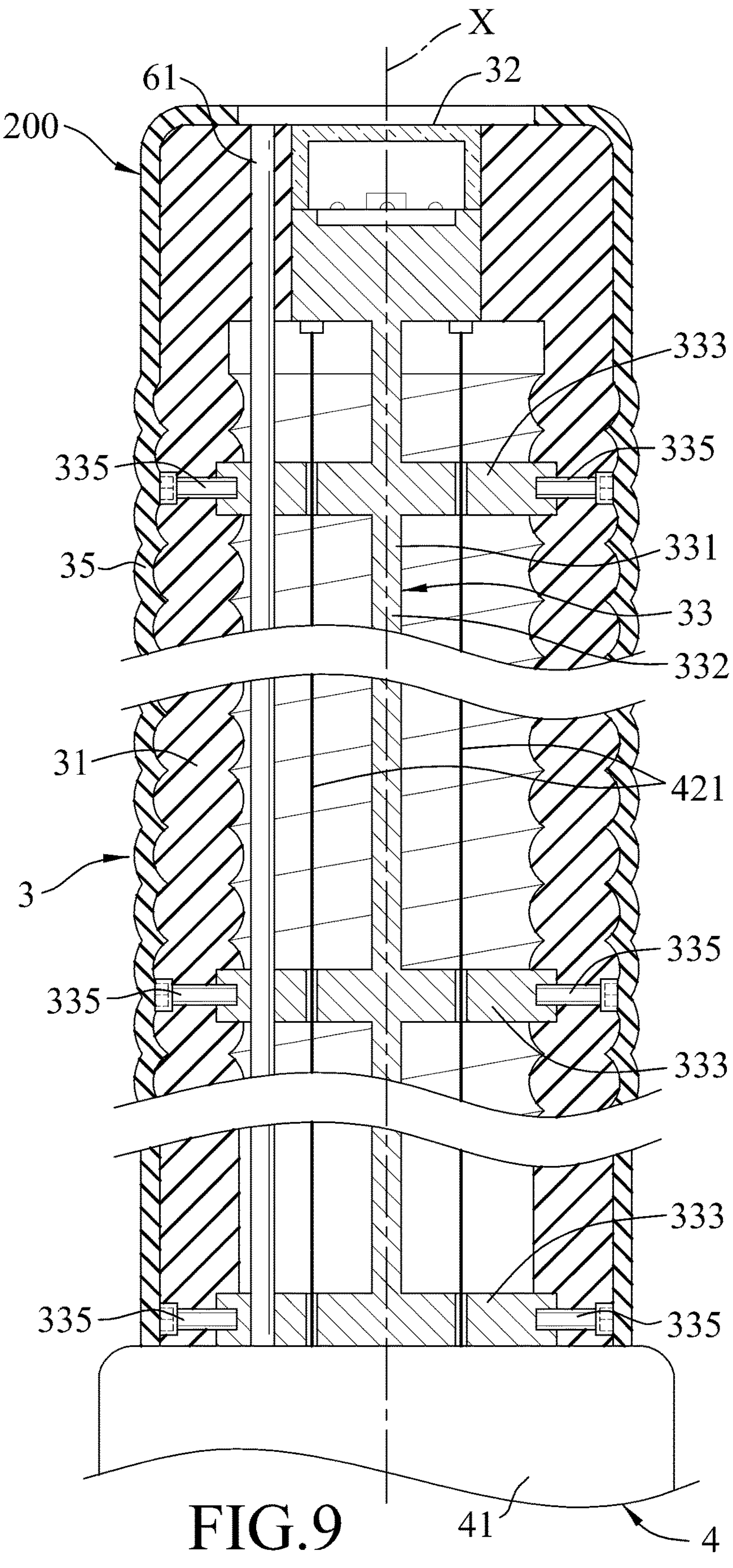
FIG. 9 is a fragmentary sectional view illustrating a tubular mechanism of another embodiment of the endoscope device according to the disclosure.

With reference to FIG. 9, in another embodiment of the endoscope device 200, the tubular mechanism 3 further includes a flexible outer sheath 35 which is sleeved on the tubular wall 311 of the elongated body 31 to conceal the fasteners 335 and to prevent removal of the fasteners 335 from the tubular mechanism 3 which may drop into the patient's body. The outer sheath 35 is a thin tubular film made of silicone rubber material, rubber material or other medical grade silicone. In this embodiment, the engaging rings 34 are dispensed with.

In the previous embodiments, the crosspiece 333 is in the form of a circular disc, and has a peripheral rim which abuts against the inner peripheral surface of the elongated body 31. In variants of the embodiments, the crosspiece 333 is in the form of a triangular plate with three arcuate corners abutting against the inner peripheral surface of the elongated body 31. The fasteners 335 extend through the elongated body 31 and are threadedly engaged with the corners of the crosspiece 333. Alternatively, the crosspiece 333 may be in the form of a rectangular plate, and has two long arcuate end surfaces abutting against the inner peripheral surface of the elongated body 31. The fasteners 335 extend through the elongated body 31 and are threadedly engaged with the arcuate end surfaces of the crosspiece 333.

Furthermore, in one embodiment, the endoscope device 200 is used with a Foley catheter with a length about 5-25 cm. The tubular mechanism 3 may be designed to be slightly longer than the Foley catheter. Due to a smaller length of the tubular mechanism 3, the bending regulating module 42 is dispensed with.

As illustrated, with the support bracket 331 securely disposed in the elongated body 31 of the tubular mechanism 3, a sufficient axial force is provided to the tubular mechanism 3 during the insertion of a medical tube or catheter with the endoscope device 200 so as to facilitate the insertion procedure of the tube or catheter.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An endoscope device comprising:

a tubular mechanism including an elongated body which has a tubular wall that defines a lumen therein and which extends along and surrounds a longitudinal axis, said tubular wall having a proximal end and a distal end opposite to each other along the longitudinal axis, a camera lens unit which is mounted at said distal end of said tubular wall to capture images of an object in front thereof, and a support unit, said support unit including a support bracket which is securely disposed in said lumen; and a control mechanism including an operating handle which is connected with said proximal end of said tubular wall, wherein the support bracket of the support unit is connected to said control mechanism at a rear end thereof and which extends from said rear end along the longitudinal axis of said elongated body to said camera lens unit, said support bracket being flexibly bendable and being controlled by said control mechanism to be bent sideways so as to bend said elongated body and steer insertion of said distal end of said tubular wall into a patient's body cavity, said support bracket having a support shaft which extends along the longitudinal axis in said lumen to be spaced apart from said tubular wall and which is bendable sideways, and at least one crosspiece in the form of a disc which extends radially from said support shaft and which is securely connected with an inner peripheral surface of said tubular wall.

2. The endoscope device of claim 1, wherein said support shaft is connected with said camera lens unit at a first end thereof.

3. The endoscope device of claim 2, wherein said camera lens unit includes a lens mounting seat securely disposed in said lumen at said distal end, said first end of said support shaft being removably connected with said lens mounting seat.

4. The endoscope device of claim 2, wherein said support shaft has a second end connected to said control mechanism.

5. The endoscope device of claim 4, wherein said tubular wall has an end wall at said distal end, and a bending section adjacent to said distal end and having threads on outer and inner peripheral surfaces thereof, said camera lens unit being exposed from said end wall of said tubular wall.

6. The endoscope device of claim 2, wherein said support shaft is in form of a hollow tubular shaft.

7. The endoscope device of claim 2, wherein said support shaft is in form of a solid shaft.

8. The endoscope device of claim 2, wherein said support shaft is in form of a spring tube.

9. The endoscope device of claim 1, wherein said support unit further includes at least one fastener which extends radially through said tubular wall and which engages with said crosspiece to fasten said crosspiece to said tubular wall.

10. The endoscope device of claim 9, wherein said tubular wall has at least one outer annular groove which is recessed from an outer peripheral surface of said tubular wall and which surrounds the longitudinal axis, said fastener extending through said outer annular groove and having a head disposed in said outer annular groove, said tubular mechanism further including an engaging ring which is disposed in said outer annular groove to conceal said fastener.

11. The endoscope device of claim 9, wherein said tubular mechanism further includes an outer sheath which is sleeved on said tubular wall to conceal said fastener.

12. The endoscope device of claim 9, wherein said fastener is a screw fastener which extends radially through said tubular wall and which is threadedly and removably engaged with said crosspiece.

13. The endoscope device of claim 1, wherein said support bracket has a plurality of said crosspieces which are securely connected with said inner peripheral surface of said tubular wall and which are spaced apart from each other along the longitudinal axis.

14. The endoscope device of claim 13, wherein said support unit further includes a plurality of fasteners each of which extends radially through said tubular wall and which engages with one of said crosspieces to fasten said crosspieces to said tubular wall.

15. The endoscope device of claim 14, wherein said tubular wall has a plurality of outer annular grooves which are recessed from an outer peripheral surface of said tubular wall, which surround the longitudinal axis, and which are spaced apart from each other along the longitudinal axis, each of said fasteners extending through one of said outer annular grooves and having a head disposed in said outer annular groove, said tubular mechanism further including a plurality of engaging rings which are respectively disposed in said outer annular grooves to conceal said fasteners.

16. The endoscope device of claim 1, wherein said crosspiece has a plurality of wire holes which are formed therethrough in a direction of the longitudinal axis, the endoscope device further comprising a suction mechanism, said suction mechanism including a suction tube which is disposed in said lumen and extends in the direction of the longitudinal axis through one of said wire holes and which has a front suction end projecting outwardly of said distal end of said tubular wall.

17. The endoscope device of claim 16, further comprising a fluid jetting mechanism, said fluid jetting mechanism including a jetting tube which is disposed in said lumen and extends in the direction of the longitudinal axis through another one of said wire holes and which has a front jetting end projecting outwardly of said distal end of said tubular wall.

18. The endoscope device of claim 1, wherein said crosspiece has a peripheral rim which is securely fitted in said inner peripheral surface of said tubular wall.

* * * * *